US00PP30795P2

(12) United States Plant Patent
Klemm et al.

(10) Patent No.: US PP30,795 P2
(45) Date of Patent: Aug. 13, 2019

(54) ***DIANTHUS* PLANT NAMED 'KLEDP18090'**

(50) Latin Name: *Dianthus caryophyllus*
Varietal Denomination: KLEDP18090

(71) Applicant: Klemm+Sohn GmbH & Co. KG, Stuttgart (DE)

(72) Inventors: Nils Klemm, Stuttgart (DE); Lena Gutbrodt, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/350,182

(22) Filed: Oct. 10, 2018

(51) Int. Cl.
*A01H 5/02* (2018.01)
*A01H 6/30* (2018.01)

(52) U.S. Cl.
USPC ..... Plt./276

(58) Field of Classification Search
USPC ..... Plt./276, 272
CPC ..... A01H 5/02; A01H 6/30
See application file for complete search history.

(56) References Cited

PUBLICATIONS

Pluto Plant Variety Database May 22, 2019. p. 1.*

* cited by examiner

*Primary Examiner* — Annette H Para
(74) *Attorney, Agent, or Firm* — Bethany R. Roahrig; Cochran Freund & Young LLC

(57) ABSTRACT

A new *Dianthus* plant particularly distinguished by light pink flowers with a dark purple pattern, and an upright habit, is disclosed.

1 Drawing Sheet

Genus and species: *Dianthus caryophyllus*.
Variety denomination: 'KLEDP18090'.

CROSS REFERENCE TO RELATED APPLICATION

A Canadian Plant Breeders Rights Application for this variety was filed on Apr. 27, 2018, Application No. 18-9428. 'KLEDP18090' has not been sold or made publicly available more than one year prior to the filing date of the present application.

BACKGROUND OF THE NEW PLANT

The present invention comprises a new and distinct variety of *Dianthus*, botanically known as *Dianthus caryophyllus*, and hereinafter referred to by the variety name 'KLEDP18090'. 'KLEDP18090' originated from a whole plant mutation of the proprietary female parent 'DCP-2012-5001' (unpatented) in March 2014, in (Netherlands).

In September 2014, 'KLEDP18090' was first vegetatively propagated by vegetative cuttings in Stuttgart Germany. 'KLEDP18090' was found to reproduce true to type in successive generations of asexual propagation in Latina, Italy via vegetative stem cuttings.

SUMMARY

The following are the most outstanding and distinguishing characteristics of this new variety when grown under normal horticultural practices in Stuttgart, Germany.

1. Light pink flowers with a dark purple pattern; and
2. An upright habit.

DESCRIPTION OF THE PHOTOGRAPH

This new *Dianthus* plant is illustrated by the accompanying photograph of a plant approximately 10 weeks old and grown in a greenhouse in Stuttgart, Germany.

The photograph shows the whole plant, including the flowers and foliage and buds and was taken in March 2016 in Stuttgart, Germany.

The colors shown are as true as can be reasonably obtained by conventional photographic procedures.

DESCRIPTION OF THE NEW VARIETY

The following detailed descriptions set forth the distinctive characteristics of 'KLEDP18090'. The data which define these characteristics were collected from asexual reproductions carried out in Stuttgart, Germany. Data was collected in April 2018 on 6-month old plants grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP18090'.

Parentage:
- *Female parent*.—The proprietary *Dianthus* variety 'DCP-2012-5001' (unpatented).

Plant:
- *Plant form*.—Upright.
- *Plant height*.—10.0 cm to 12.0 cm.
- *Plant diameter or spread*.—14.0 cm to 16.0 cm.
- *Propagation type*.—Vegetative cuttings, stem cutting.

*Time to produce a rooted young plant.*—10 to 14 days.
*Root description.*—White, fine.
*Rooting habit (shape).*—Lanceolate.

Lateral branches:
*Number of lateral branches.*—10.
*Strength.*—Normal.
*Length.*—7.0 cm to 9.0 cm.
*Diameter.*—2.0 mm to 4.0 mm.
*Internode length.*—0.4 mm to 0.6 mm.
*Number of internodes per branch/stem.*—4.
*Node length.*—0.3 cm.
*Node diameter.*—0.3 cm.
*Texture.*—Smooth.
*Color.*—RHS N137B.
*Branch/stem appearance.*—Solid.

Foliage:
*Arrangement.*—Opposite.
*Length.*—4.0 cm to 6.0 cm.
*Width.*—0.6 cm to 0.8 cm.
*Shape.*—Lanceolate.
*Apex.*—Acute.
*Base.*—Obtuse.
*Margin.*—Entire.
*Texture (both upper and lower surfaces).*—Smooth.
*Immature leaf color.*—Upper surface: RHS 143A. Lower surface: RHS 143B.
*Mature leaf color.*—Upper surface: RHS 139A. Lower surface: RHS N137B.
*Venation pattern.*—Parallel.
*Venation color.*—Upper surface: RHS 139A. Lower surface: RHS N137B.

Flowers:
*Flower type and habit.*—Double flower, small sprays.
*Fragrance.*—Present, typical of a carnation.
*Natural flowering season.*—Spring to fall.
*Position of flowers relative to the foliage.*—Slightly above.
*Number of flowers per spray.*—2 to 4.
*Flower longevity on the plant.*—10 to 12 days.
*Buds.*—Length: 1.8 cm to 2.0 cm. Diameter: 0.8 cm to 1.0 cm. Shape: Elliptic. Color: apical part: Apical part is RHS 137A and basal part is RHS 143C. Extrusion of the styles at the bud stage: Absent.
*Corolla.*—Quantity of petals and arrangement: 15 to 20 in whorls. Corolla height: 1.5 cm to 2.0 cm. Corolla diameter: 3.5 cm. Petal length: 2.5 cm. Petal width: 1.4 cm to 1.6 cm. Petal shape: Spoon-shaped. Petal apex: Obtuse. Petal base: Acute. Petal margin: Crenate. Depth of petal margin: Medium. Petal texture (both upper and lower surfaces): Smooth. Petal luster (both surfaces): Dull. Petal color: Immature: Upper surface: Basal part is RHS 59A and RHS apical part is 62C. Lower surface: Stripes are RHS 65A and ground color is RHS 69D. Mature: Upper surface: Basal part is RHS 64B and apical part is RHS 69D. Lower surface: RHS 69D.
*Calyx.*—Quantity of sepals and arrangement: Composed of 5 sepals, fused. Shape: Campanulate. Calyx height: 1.8 cm to 2.0 cm. Calyx diameter (at the apex): 0.8 cm to 1.0 cm. Sepal texture (both upper and lower surfaces): Smooth. Sepal color: Upper surface: RHS 137A. Lower surface: RHS 137D. Sepal length: 1.5 cm. Sepal diameter: 1.1 cm. Sepal apex: Acute. Sepal base: Obtuse. Sepal margin: Entire. Sepal luster: Upper surface: Light and shinny. Lower surface: Dull.

Peduncles:
*Length.*—12.0 cm to 14.0 cm.
*Diameter.*—0.2 cm.
*Strength.*—Moderate.
*Texture.*—Smooth.
*Color.*—RHS N137A.

Reproductive organs:
*Stamens.*—Quantity per flower: 3 to 5. Filament length: 0.5 cm to 0.7 cm. Filament color: RHS N155B. Anther length: 0.1 cm. Anther diameter: 0.05 cm. Anther color: RHS N155B. Pollen amount: Sparse.
*Pistils.*—Quantity per flower: 1. Pistil length: 1.2 cm to 1.6 cm. Style length: 0.8 cm to 1.0 cm. Style color: RHS N155B. Stigma shape: Filamentous. Stigma color: RHS N155B. Ovary size: 0.4 cm to 0.6 cm. Ovary shape: Oval. Ovary color: RHS 144C.

Fruit and seed set: Seed is sometimes observed, but no information on the seed is available.

Disease and pest/insect resistance: No disease and pest/insect resistance observed.

COMPARISON WITH PARENTAL LINE AND KNOWN VARIETY

'KLEDP18090' is distinguished from its female parent as described in Table 1.

TABLE 1

Comparison with Parental Line

| Characteristic | 'KLEDP18090' | Female Parent 'DCP-2012-5001' |
|---|---|---|
| Flower color contrast in Spring | Very good; bicolored from the beginning of flowering | Less contrast between the two colors, almost light pink in color |

'KLEDP18090' can be compared to the commercial *Dianthus* variety 'Oscar Purple Wings', also known as 'KLEDP14206' (U.S. application Ser. No. 14/120,456). Differences between the varieties are described in Table 2.

TABLE 2

Comparison with Similar Variety

| Characteristic | 'KLEDP18090' | 'Oscar Purple Wings' |
|---|---|---|
| Flower color | Light pink with a dark purple pattern | Purple with a dark purple pattern |

We claim:

1. A new and distinct variety of *Dianthus* plant designated 'KLEDP18090' as illustrated and described herein.

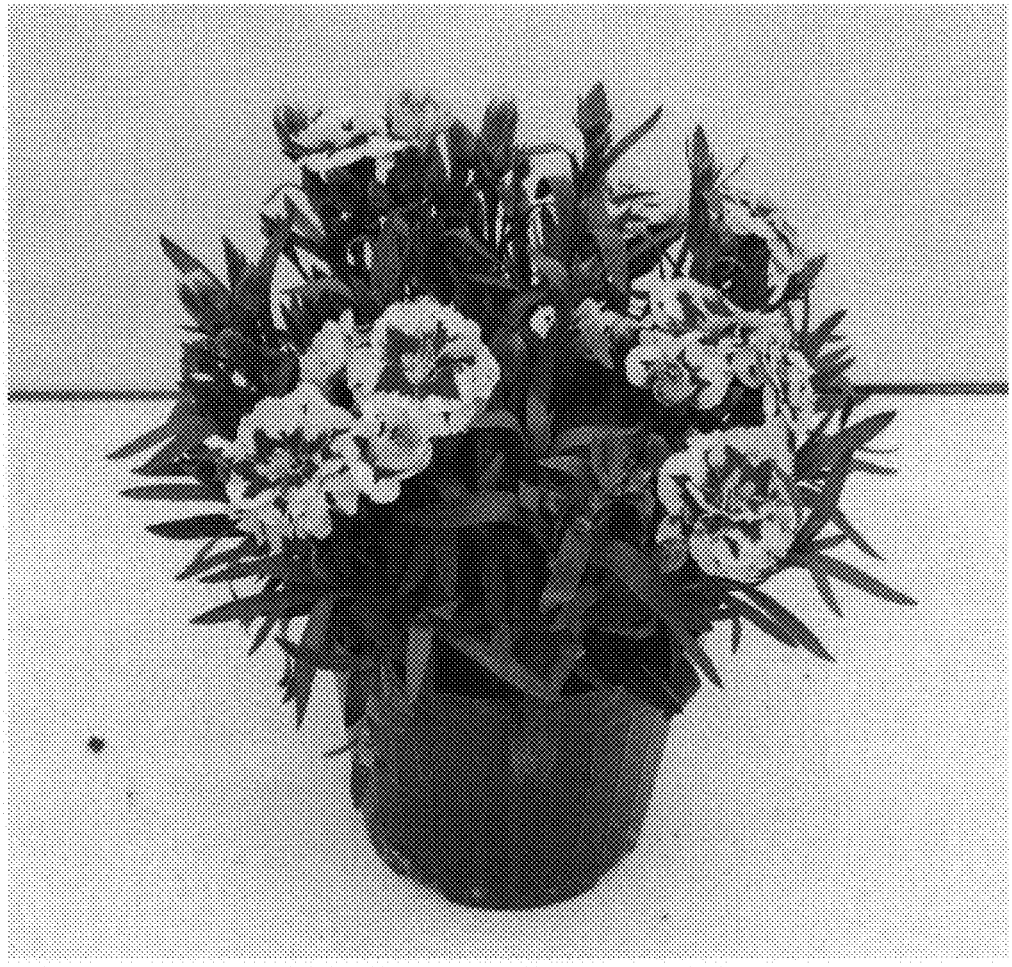

* * * * *